US010960156B2

(12) United States Patent
Huang et al.

(10) Patent No.: US 10,960,156 B2
(45) Date of Patent: Mar. 30, 2021

(54) NEBULIZER AND BREATH-ACTUATED NEBULIZATION METHOD

(71) Applicant: ENCHANT TEK. CO., LTD., Dongshan Township, Yilan County (TW)

(72) Inventors: Mu-Hua Huang, Dongshan Township, Yilan County (TW); Chun-Hung Chen, Dongshan Township, Yilan County (TW); Ling-Ling Leonard Lin, Dongshan Township, Yilan County (TW)

(73) Assignee: ENCHANT TEK. CO., LTD., Dongshan Township, Yilan County (TW)

( * ) Notice: Subject to any disclaimer, the term of this patent is extended or adjusted under 35 U.S.C. 154(b) by 220 days.

(21) Appl. No.: 16/033,513

(22) Filed: Jul. 12, 2018

(65) Prior Publication Data

US 2019/0099564 A1 Apr. 4, 2019

(30) Foreign Application Priority Data

Sep. 29, 2017 (TW) ................................ 106133567
May 5, 2018 (TW) ................................ 107115357

(51) Int. Cl.
*A61M 15/00* (2006.01)
*A61M 16/20* (2006.01)
(Continued)

(52) U.S. Cl.
CPC ........ *A61M 15/0091* (2013.01); *A61M 11/02* (2013.01); *A61M 11/06* (2013.01); *A61M 15/002* (2014.02); *A61M 15/009* (2013.01); *A61M 16/14* (2013.01); *A61M 16/209* (2014.02); *B05B 1/265* (2013.01); *B05B 7/0012* (2013.01); *B05B 7/1272* (2013.01);
(Continued)

(58) Field of Classification Search
CPC .... A61M 11/00; A61M 11/002; A61M 11/02; A61M 11/06; A61M 15/002; A61M 15/009; A61M 15/0091; A61M 16/14; A61M 16/209; B05B 1/265; B05B 7/0012; B05B 7/1272; B05B 7/2435
See application file for complete search history.

(56) References Cited

U.S. PATENT DOCUMENTS 6,044,841 A * 4/2000 Verdun .................. A61M 11/06
128/200.18
2002/0157663 A1* 10/2002 Blacker ................ A61M 11/007
128/200.21
(Continued)

*Primary Examiner* — Joseph D. Boecker
(74) *Attorney, Agent, or Firm* — Muncy, Geissler, Olds and Lowe, P.C.

(57) ABSTRACT

A nebulizer comprises a housing, a closed pressure system, at least one pressure relief mechanism and a nebulization mechanism. The housing comprises a nozzle, and the nozzle comprises an outlet portion and an inlet portion communicated with a pressurized gas source. The closed pressure system comprises at least one gas inlet and a gas outlet. The at least one pressure relief mechanism is disposed on the at least one gas inlet. The nebulization mechanism is capable of moving to a nebulization position. An interior pressure in the closed pressure system is changed by the at least one pressure relief mechanism to control the nebulization mechanism for nebulization.

16 Claims, 13 Drawing Sheets

(51) Int. Cl.

| | |
|---|---|
| ***A61M 11/06*** | (2006.01) |
| ***A61M 11/02*** | (2006.01) |
| ***A61M 16/00*** | (2006.01) |
| ***B05B 1/26*** | (2006.01) |
| ***B05B 7/00*** | (2006.01) |
| ***B05B 7/24*** | (2006.01) |
| ***B05B 7/12*** | (2006.01) |
| ***A61M 16/14*** | (2006.01) |

(52) U.S. Cl.
CPC ....... *B05B 7/2435* (2013.01); *A61M 15/0021* (2014.02); *A61M 2016/0015* (2013.01)

(56) References Cited

U.S. PATENT DOCUMENTS

| | | | | |
|---|---|---|---|---|
| 2003/0005929 | A1* | 1/2003 | Grychowski ....... | A61M 15/008 128/203.12 |
| 2009/0217923 | A1* | 9/2009 | Boehm ............. | A61M 15/0091 128/200.14 |
| 2013/0327323 | A1* | 12/2013 | Rubin ............... | A61M 16/1055 128/200.18 |
| 2016/0228656 | A1* | 8/2016 | Vasandani ......... | A61M 15/0091 |
| 2018/0008789 | A1* | 1/2018 | Alizoti ................ | A61M 16/208 |

* cited by examiner

NEBULIZER AND BREATH-ACTUATED NEBULIZATION METHOD

CROSS-REFERENCE TO RELATED APPLICATION

This application claims the priority benefits of Taiwan Patent Application Nos. 106133567, filed on Sep. 29, 2017, and 107115357, filed on May 5, 2018. The entirety of the above-mentioned patent applications are hereby incorporated by reference herein and made a part of this specification.

BACKGROUND

1. Field of the Invention

The present disclosure generally relates to a nebulizer, and more particularly to a nebulizer capable of being actuated by breathing. The present disclosure further relates to a breath-actuated nebulization method by the nebulizer.

2. Description of Related Art

Because air pollution is becoming more serious, environmental allergens are also increasing significantly such that respiratory problems for modern people are easily triggered. A patient can control continuously non-sudden respiratory symptoms with oral medications. However, for sudden respiratory symptoms, such as asthma and dyspnea, to relieve the patient's discomfort in time, the patient usually inhales liquid drugs by oronasal breathing such that the liquid drugs enter the respiratory system directly and quickly for effective treatment. To facilitate the inhalation of the liquid drugs by the patient, a nebulizer is generally used to nebulize the liquid drugs, and the nebulized liquid drugs are in the form an aerosol that is capable of entering the respiratory system with inspiration of the patient.

At present, some nebulizers are designed to manually control the nebulization of the liquid drugs. Although users can control the nebulization of the liquid drugs of the nebulizers when they are in need, it is inconvenient that the users must manually operate the nebulizers for each inspiration at the same time. In addition, currently available automatic nebulizers can continuously nebulize the liquid drugs, so they are more convenient in operation than the aforementioned manual nebulizers. However, the users cannot actively stop the nebulization of the liquid drugs of the automatic nebulizers until the gas supply is stopped. Even if the users exhale, the nebulization of the liquid drugs is still performed, which results in the waste of the liquid drugs.

Accordingly, there is a need to provide a nebulizer capable of ameliorating the above defects for easy operation by users.

SUMMARY

An object of this disclosure is to provide a nebulizer capable of being actuated by breathing.

To achieve the aforesaid and other objects, a nebulizer of this disclosure comprises a housing, a closed pressure system, at least one pressure relief mechanism and a nebulization mechanism. The housing comprises a nozzle, and the nozzle comprises an outlet portion and an inlet portion communicated with a pressurized gas source. The closed pressure system comprises at least one gas inlet and a gas outlet. The at least one pressure relief mechanism is disposed on the at least one gas inlet. The nebulization mechanism is capable of moving to a nebulization position. An interior pressure in the closed pressure system is changed by the at least one pressure relief mechanism.

In one embodiment of this disclosure, the closed pressure system further comprises an airtight chamber and a gas channel, and the airtight chamber is communicated with the gas outlet via the gas channel.

In one embodiment of this disclosure, the nebulization mechanism is actuated to move to the nebulization position by the at least one pressure relief mechanism.

In one embodiment of this disclosure, the housing further comprises a liquid storage chamber, a liquid channel and a liquid outlet; the liquid storage chamber is communicated with the liquid outlet via the liquid channel; and the gas channel and the liquid channel are not communicated with each other.

In one embodiment of this disclosure, the gas outlet and the liquid outlet are arranged at the same side of the outlet portion.

In one embodiment of this disclosure, the nebulization mechanism comprises a block portion, wherein when the nebulization mechanism moves to the nebulization position, a liquid is driven by the pressurized gas source to impact the block portion.

In one embodiment of this disclosure, the closed pressure system further comprises an actuating element connected with the nebulization mechanism.

In one embodiment of this disclosure, the actuating element is an elastically deformable element.

In one embodiment of this disclosure, the actuating element is capable of maintaining the nebulization mechanism at the nebulization position when a pressurized gas is provided by the pressurized gas source.

This disclosure further comprises a nebulizer in communication with a pressurized gas source and storing a liquid. The nebulizer comprises a differential pressure forming structure, an airtight unit and a nebulization mechanism. The differential pressure forming structure is used for inputting a pressurized gas from the pressurized gas source and forming a pressure difference at an outlet portion. The airtight unit is in gas communication with the outlet portion. The nebulization mechanism is capable of moving relative to the outlet portion of the differential pressure forming structure. The airtight unit is configured to actuate the nebulization mechanism in response to the pressure difference.

In one embodiment of this disclosure, the nebulizer further comprises a liquid transmission unit in liquid communication with a position adjacent to the outlet portion, and the liquid transmission unit is configured to transmit the liquid to the outlet portion by the pressurized gas in the presence of a pressure difference.

In one embodiment of this disclosure, the nebulization mechanism is actuated to move to a nebulization position or a non-nebulization position, and the nebulization mechanism is capable of nebulizing the liquid into an aerosol at the nebulization position when the pressurized gas is provided by the pressurized gas source.

In one embodiment of this disclosure, the airtight unit comprises an airtight chamber and a gas channel, and the gas channel is connected with the airtight chamber.

In one embodiment of this disclosure, the liquid transmission unit comprises a liquid storage chamber and a liquid channel connected with the liquid storage chamber.

In one embodiment of this disclosure, the airtight unit and the liquid transmission unit are not communicated with each other.

In one embodiment of this disclosure, gas is removed from the airtight unit by a pressure difference, and an interior gas pressure of the airtight unit is maintained as a first pressure.

In one embodiment of this disclosure, the airtight unit further comprises at least one pressure relief mechanism for releasing the interior gas pressure of the airtight unit to a second pressure.

In one embodiment of this disclosure, the nebulization mechanism moves close to the outlet portion to nebulize the liquid into the aerosol when the nebulization mechanism moves to the nebulization position from the non-nebulization position, wherein the nebulization mechanism moves away from the outlet portion when the nebulization mechanism moves to the non-nebulization position from the nebulization position.

This disclosure further comprises a breath-actuated nebulization method. The method comprises: providing a nebulizer comprising a housing having a nozzle and receiving a liquid therein; introducing a pressurized gas from an inlet portion of the nozzle and producing a pressure difference at an outlet portion of the nozzle; removing gas from an airtight unit in the housing via a gas channel by the pressure difference to decrease an interior gas pressure of the airtight unit; and introducing air into the airtight unit with inspiration to increase the interior gas pressure of the airtight unit such that the liquid is drawn through a liquid channel by the pressure difference.

In one embodiment of this disclosure, the liquid impacts a nebulization mechanism along with the pressurized gas to produce an aerosol.

In one embodiment of this disclosure, the nebulization mechanism moves close to the outlet portion to nebulize the liquid into the aerosol when the nebulization mechanism moves to a nebulization position from a non-nebulization position, and the nebulization mechanism moves away from the outlet portion when the nebulization mechanism moves to the non-nebulization position from the nebulization position.

In one embodiment of this disclosure, the air is introduced into the airtight unit by a pressure relief mechanism.

BRIEF DESCRIPTION OF THE DRAWINGS

The accompanying drawings are included to provide a further understanding of the invention and are incorporated in and constitute a part of this specification. The drawings illustrate embodiments of the invention and, together with the descriptions, serve to explain the principles of the invention.

DETAILED DESCRIPTION OF THE EMBODIMENTS

Since various aspects and embodiments are merely exemplary and not limiting, after reading this specification, those skilled in the art will appreciate that other aspects and embodiments are possible without departing from the scope of the disclosure. Other features and benefits of any one or more of the embodiments will be apparent from the following detailed description and the claims.

The indefinite articles "a" or "an" are employed to describe elements and components described herein merely for convenience and to give a general sense of the scope of the disclosure. Accordingly, this description should be read to include one or at least one and the singular also includes the plural unless it is obvious that it is meant otherwise.

As used herein, the terms "first," "second," and the like are used for distinguishing between or referring to identical or similar elements or structures and not necessarily for describing a sequential or chronological order thereof. It should be understood that the terms so used are interchangeable under appropriate circumstances or configurations.

As used herein, the terms "comprises," "comprising," "includes," "including," "has," "having" or any other variations thereof are intended to cover a non-exclusive inclusion. For example, a component, structure, article, or apparatus that comprises a list of elements is not necessarily limited to only those elements but may include other elements not expressly listed or inherent to such component, structure, article, or apparatus.

Figure 1:
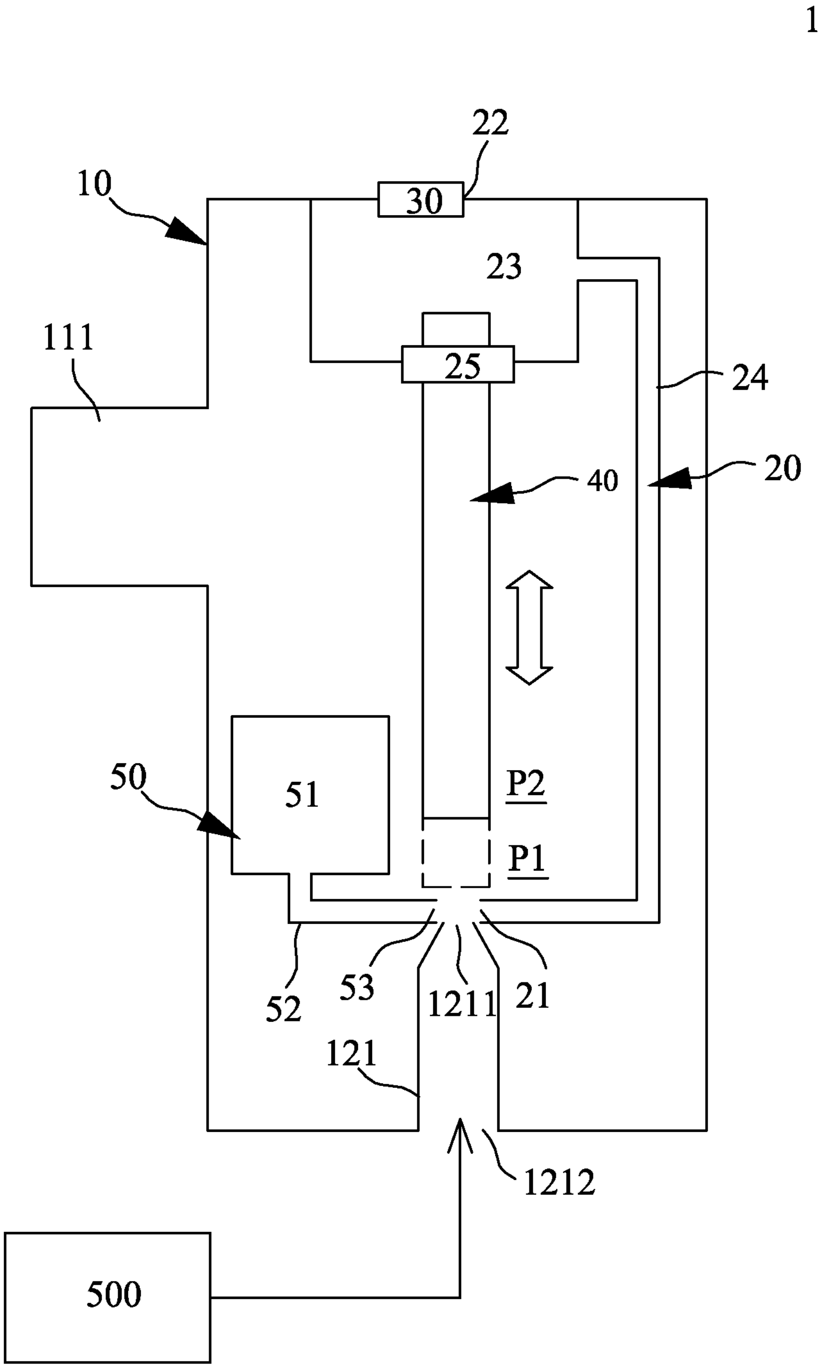
FIG. 1 illustrates a schematic diagram of a nebulizer of this disclosure.

Please refer to FIG. 1, which illustrates a schematic diagram of a nebulizer of this disclosure. As illustrated in FIG. 1, a pressurized gas from a pressurized gas source 500 is inputted into the nebulizer 1 of this disclosure, and an interior pressure change is formed when a patient breathes by the nebulizer 1 of this disclosure, such that nebulization of a liquid in the nebulizer 1, such as a drug, is controllable. The pressurized gas source 500 may be at least one of a blower, a motor and an air pump, and the pressurized gas may be pressurized oxygen or air, but this disclosure is not limited thereto.

As illustrated in FIG. 1, the nebulizer 1 of this disclosure comprises a housing 10, a closed pressure system 20, at least one pressure relief mechanism 30 and a nebulization mechanism 40. The housing 10 comprises a branch pipe 111 and a nozzle 121. The branch pipe 111 is configured for being held in a mouth of the patient for breathing. The nozzle 121 comprises an outlet portion 1211 and an inlet portion 1212. The outlet portion 1211 is configured inside the housing 10, and the inlet portion 1212 is communicated with the pressurized gas source 500 for inputting the pressurized gas. The term "nozzle" is defined as a cross-section area of the nozzle 121 that is gradually reduced towards the outlet portion 1211 such that a minimum cross-section area of the nozzle 121 is formed at the outlet portion 1211. Accordingly, when the pressurized gas is outputted through the outlet portion 1211 of the nozzle 121, a pressure difference is produced at the outlet portion 1211 by the decrease in the cross-section area of a gas path based on Bernoulli's principle. In addition, the nebulizable liquid is stored in the housing 10.

The closed pressure system 20 is disposed in the housing 10. The closed pressure system 20 comprises a gas outlet 21 and at least one gas inlet 22. The gas outlet 21 is adjacent to the outlet portion 1211 to be an outlet of an interior gas in the closed pressure system 20. Each gas inlet 22 is an inlet for introducing external gas into the closed pressure system 20. The term "adjacent" is defined as the gas outlet 21 being configured in a range of a pressure difference formed at the outlet portion 1211. The closed pressure system 20 further comprises an airtight chamber 23 and a gas channel 24. The at least one gas inlet 22 is disposed at one side of the airtight chamber 23 such that the airtight chamber 23 is communicated with the external air via the at least one gas inlet 22. The airtight chamber 23 is communicated with the gas outlet 21 via the gas channel 24. In other words, one end of the gas channel 24 is communicated with the airtight chamber 23, and the other end of the gas channel 24 forms the gas outlet 21 at a position adjacent to the outlet portion 1211.

The at least one pressure relief mechanism 30 is disposed correspondingly on the at least one gas inlet 22. The pressure relief mechanism 30 is a control means that determines whether the external gas enters the closed pressure system 20. For example, the pressure relief mechanism 30 may be a check valve or other components.

The nebulization mechanism 40 is disposed in the housing 10. The nebulization mechanism 40 is actuatable to move to a nebulization position P1 (the position shown as dotted lines in FIG. 1) or a non-nebulization position P2 relative to the outlet portion 1211 of the nozzle 121 by the interior pressure change of the closed pressure system 20. When the nebulization mechanism 40 moves to the nebulization position P1, the nebulizer 1 of this disclosure nebulizes the liquid drug stored in the housing 10. Oppositely, when the nebulization mechanism 40 moves to the non-nebulization position P2, nebulization by the nebulizer 1 of this disclosure is stopped.

When the at least one pressure relief mechanism 30 is changed to an unopened state, a closed space is formed in the closed pressure system 20. Therefore, the nebulizer 1 of this disclosure forms the pressure difference at the outlet portion 1211 by inputting the pressurized gas, and the gas stored in the closed pressure system 20 is removed from the gas outlet 21 so as to reduce the interior pressure of the closed pressure system 20. At this moment, the nebulization mechanism 40 is actuated to move to the non-nebulization position P2. When the at least one pressure relief mechanism 30 is changed to an opened state, the interior pressure of the closed pressure system 20 is less than the external air pressure. Therefore, the external air may be introduced into the closed pressure system 20 through each gas inlet 22 to eliminate the closed space, such that the interior pressure of the closed pressure system 20 is increased. At this moment, the nebulization mechanism 40 is actuated to move to the nebulization position P1. Accordingly, the interior pressure of the closed pressure system 20 is changeable by the at least one pressure relief mechanism 30 such that the nebulization mechanism 40 is actuated to move to nebulize or not to nebulize the liquid.

Furthermore, the nebulizer 1 of this disclosure further comprises a liquid transmission unit 50. The liquid transmission unit 50 is disposed in the housing 10. The liquid transmission unit 50 comprises a liquid storage chamber 51, a liquid channel 52 and a liquid outlet 53, and the liquid storage chamber 51 is communicated with the liquid outlet 53 via the liquid channel 52. The liquid outlet 53 is disposed at a position adjacent to the outlet portion 1211 to be an outlet of the liquid in the liquid transmission unit 50. The term "adjacent" is defined as the liquid outlet 53 being configured in a range of a pressure difference formed at the outlet portion 1211. In other words, one end of the liquid channel 52 is communicated with the liquid storage chamber 51, and the other end of the liquid channel 52 forms the liquid outlet 53 at the position adjacent to the outlet portion 1211.

Similarly, when the nebulizer 1 of this disclosure forms the pressure difference at the outlet portion 1211 by inputting the pressurized gas, the liquid stored in the liquid transmission unit 50 is drawn from the liquid outlet 53 by the pressure difference if the liquid channel 52 is not obstructed. The drawn liquid may be moved with the pressurized gas jetted from the outlet portion 1211. Once the liquid moved with the pressurized gas is blocked by an object and impacts the object, the liquid is distributed into an aerosol for nebulization. Therefore, the nebulization mechanism 40 may be the above object for blocking the pressurized gas and the liquid or may obstruct the liquid channel 52 or maintain the communication of the liquid channel 52 according to the different positions of the nebulization mechanism 40. In other words, nebulization of the liquid can be driven or stopped by controlling the nebulization mechanism 40.

The gas channel 24 of the closed pressure system 20 and the liquid channel 52 of the liquid transmission unit 50 are not communicated with each other. In other words, the gas channel 24 and the liquid channel 52 are independently fluid transmission paths, and the gas outlet 21 and the liquid outlet 53 are disposed independently. Therefore, the gas transmission of the closed pressure system 20 and the liquid transmission of the liquid transmission unit 50 are not influenced by each other.

Further, the closed pressure system 20 further comprises an actuating element 25. The actuating element 25 is adjacent to the airtight chamber 23, and the actuating element 25 is connected with the nebulization mechanism 40. When the actuating element 25 moves, an operable linkage is formed between the nebulization mechanism 40 and the actuating element 25 to actuate the nebulization mechanism 40 to move. The actuating element 25 may be an elastically deformable element, such as an elastic valve. Therefore, the actuating element 25 may be deformed according to the pressure change in the airtight chamber 23 such that the nebulization mechanism 40 is actuated to move to the nebulization position P1 or the non-nebulization position P2. Furthermore, sufficient downward support for the nebulization mechanism 40 is provided by the deformation of the actuating element 25. When the pressurized gas is provided by the pressurized gas source 500, the nebulization mechanism 40 actuated by the actuating element 25 to move to the nebulization position P1 is capable of resisting the pressurized gas to be maintained at the nebulization position P1 until the nebulization mechanism 40 is actuated by the actuating element 25 to leave the nebulization position P1 according to the pressure change in the airtight chamber 23. In one embodiment of this disclosure, the downward support for the nebulization mechanism 40 provided by the actuating element 25 is about 30 grams to 50 grams, but this disclosure is not limited thereto.

Figure 2:
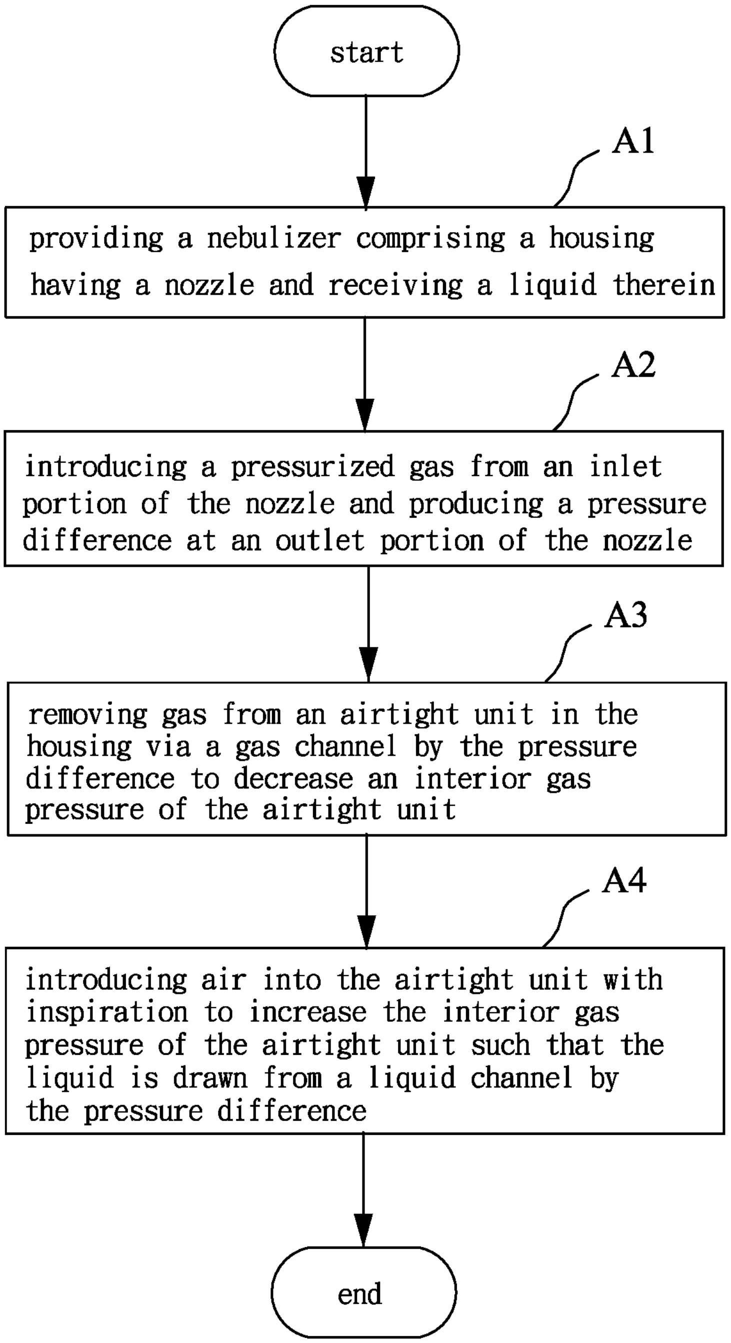
FIG. 2 illustrates a flowchart of a breath-actuated nebulization method of this disclosure.

Refer to FIG. 1 and FIG. 2. FIG. 2 illustrates a flowchart of a breath-actuated nebulization method of this disclosure. The breath-actuated nebulization method of this disclosure is capable of being used for the nebulizer 1 of this disclosure or other nebulizers with similar structural characters. As illustrated in FIG. 2, the breath-actuated nebulization method of this disclosure comprises Steps A1 to A4, which are exemplified in detail below.

Step A1: providing a nebulizer comprising a housing having a nozzle and receiving a liquid therein.

First, the nebulizer 1 of this disclosure is provided to the patient. The housing 10 of the nebulizer 1 of this disclosure comprises the branch pipe 111 and the nozzle 121, and the nebulizable liquid, such as a drug, is pre-stored in the liquid storage chamber 51 of the housing 10. In an initial state, the nebulization mechanism 40 is at the nebulization position P1.

Step A2: introducing a pressurized gas from an inlet portion of the nozzle and producing a pressure difference at an outlet portion of the nozzle.

After the nebulizer 1 is provided in Step A1, the inlet portion 1212 of the nozzle 121 is communicated with the pressurized gas source 500, and the pressurized gas is introduced from the inlet portion 1212 of the nozzle 121 by the pressurized gas source 500 and is jetted from the outlet portion 1211 of the nozzle 121. The pressure difference is produced by the pressurized gas at the outlet portion 1211 of the nozzle 121 according to the structure of the nozzle 121.

Step A3: removing gas from an airtight unit in the housing via a gas channel by the pressure difference to decrease an interior gas pressure of the airtight unit.

After the pressure difference is produced in Step A2, the gas in the airtight chamber 23 of the housing 10 is removed via a gas channel 24 by the pressure difference to decrease the interior gas pressure of the airtight chamber 23 because the pressure of the outlet portion 1211 is less than the interior pressure of the airtight chamber 23 and the gas outlet 21 is configured in the range of the pressure difference formed at the outlet portion 1211. At this moment, the nebulization mechanism 40 is actuated to move to the non-nebulization position P2 from the nebulization position P1 by the decrease in the interior gas pressure of the airtight chamber 23, such that the nebulization mechanism 40 moves away from the outlet portion 1211.

Step A4: introducing air into the airtight unit with inspiration to increase the interior gas pressure of the airtight unit such that the liquid is drawn through a liquid channel by the pressure difference.

After the interior gas pressure of the airtight unit is decreased in Step A3, the branch pipe 111 is placed into the mouth of the patient for breathing. Every time the patient inspires, the at least one pressure relief mechanism 30 is changed to the opened state by a suction of the inspiration, and the external air is introduced into the airtight chamber 23 through the pressure relief mechanism 30 from the gas inlet 22, such that the interior pressure of the airtight chamber 23 is increased. At this moment, the nebulization mechanism 40 is actuated to move to the nebulization position P1 from the non-nebulization position P2 by the increase in the interior gas pressure of the airtight chamber 23 such that the nebulization mechanism 40 moves close to the outlet portion 1211. The nebulization mechanism 40 at the nebulization position P1 is capable of maintaining the communication of the liquid channel 52 while the object is additionally configured for blocking the pressurized gas and the liquid, or is capable of being the object for blocking the pressurized gas and the liquid while the liquid channel 52 has been communicated. Accordingly, the liquid stored in the liquid storage chamber 51 is drawn through the liquid channel 52 by the pressure difference which is formed at the liquid outlet 53 after the pressurized gas is blocked. The liquid drawn from the liquid outlet 53 is attracted to the outlet portion 1211 such that the liquid is moved with the pressurized gas to impact the nebulization mechanism 40 or the other objects capable of blocking the pressurized gas and the liquid to produce an aerosol.

Oppositely, every time the patient exhales, the at least one pressure relief mechanism 30 is changed to the unopened state, and the external air cannot be introduced into the airtight chamber 23 from the gas inlet 22, such that the airtight unit 23 forms the closed space again. The gas in the airtight chamber 23 is removed again via the gas channel 24 by the pressure difference to decrease the interior gas pressure of the airtight chamber 23. At this moment, the nebulization mechanism 40 is actuated to move to the non-nebulization position P2 from the nebulization position P1 such that the nebulization mechanism 40 moves away from the outlet portion 1211. The nebulization mechanism 40 obstructs the communication of the liquid channel 52 or unblocks the pressurized gas to form the pressure difference at the liquid outlet 53, such that the liquid cannot be drawn, thereby stopping the production of aerosol.

Therefore, according to the breath-actuated nebulization method of this disclosure, the patient only uses the nebulizer 1 of this disclosure to breathe normally, and nebulization of the liquid is produced corresponding to the inspiration of the patient and is stopped corresponding to the exhalation of the patient. It is more convenient in operation and avoids unnecessary waste of the liquid drug.

Figure 3:
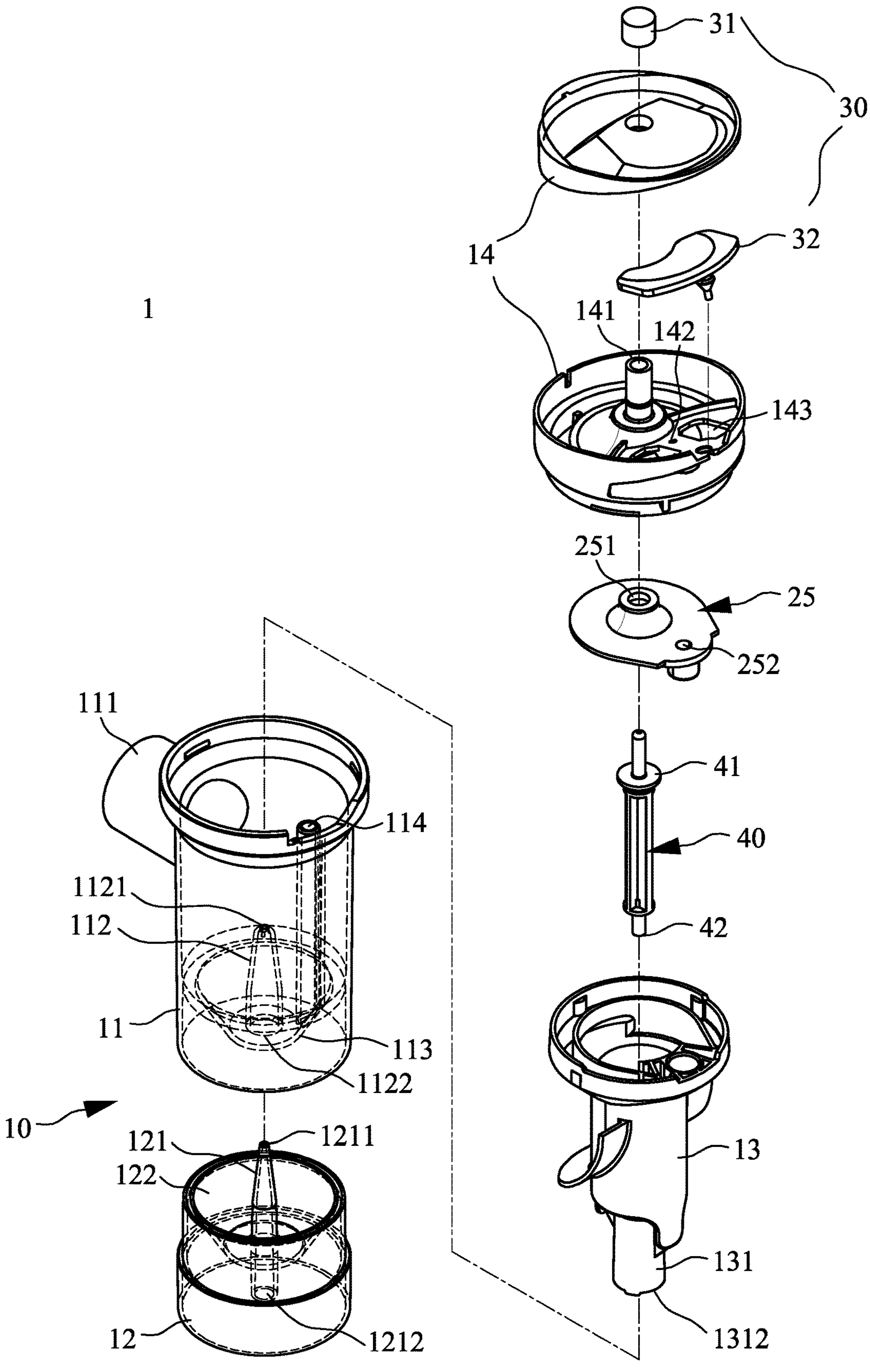
FIG. 3 illustrates an exploded view of a first embodiment of the nebulizer of this disclosure.
Figure 4:
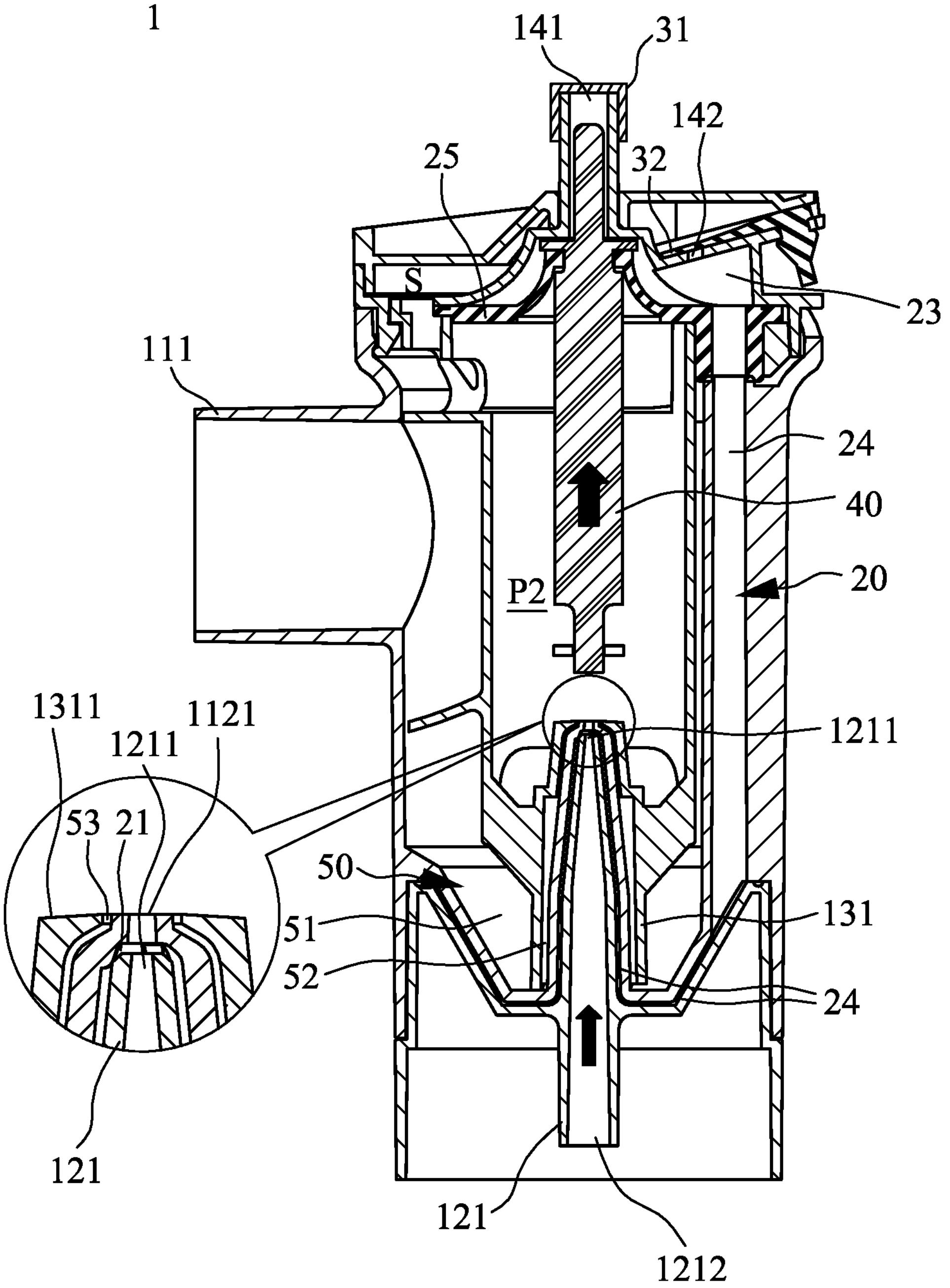
FIG. 4 illustrates a cross-sectional view of the nebulization mechanism of the first embodiment of the nebulizer of this disclosure at the non-nebulization position.
Figure 5A:
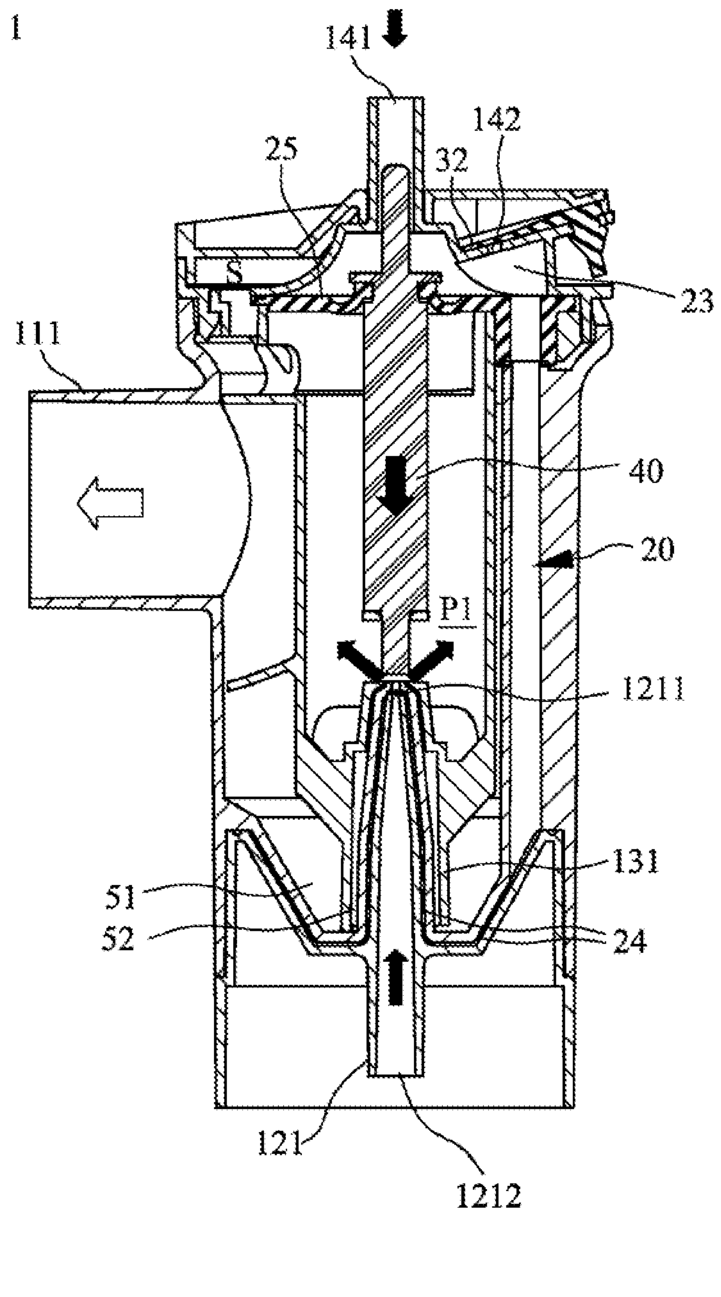
FIGS. 5A-5B illustrate cross-sectional views of the nebulization mechanism of the first embodiment of the nebulizer of this disclosure at the nebulization position.
Figure 5B:
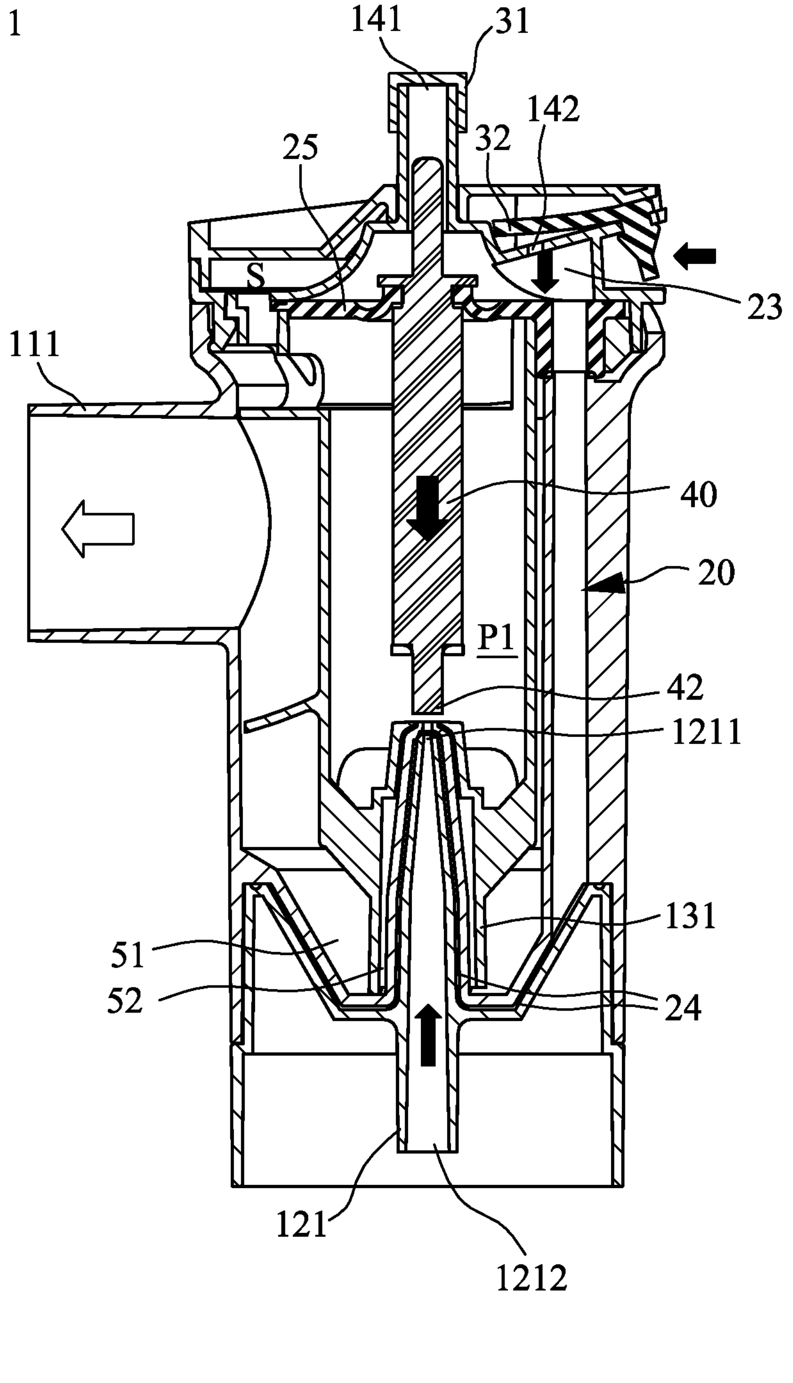

Each embodiment of the nebulizer of this disclosure is explained by several different structural designs according to the aspect of FIG. 1. Please refer to FIG. 3 to FIG. 5B. FIG. 3 illustrates an exploded view of a first embodiment of the nebulizer 1 of this disclosure, FIG. 4 illustrates a cross-sectional view of the nebulization mechanism 40 of the first embodiment of the nebulizer 1 of this disclosure at the non-nebulization position P2, and FIGS. 5A-5B illustrate cross-sectional views of the nebulization mechanism 40 of the first embodiment of the nebulizer 1 of this disclosure at the nebulization position P1. As illustrated in FIG. 3 to FIG. 5B, the nebulizer 1 of this disclosure comprises a housing 10, a closed pressure system 20, at least one pressure relief mechanism 30 and a nebulization mechanism 40. The housing 10 comprises a base case 11, a lower case 12, an inner case 13 and an upper cover 14. An inner space is formed in the base case 11, and the base case 11 comprises a branch pipe 111 communicated with the inner space and a nozzle cover 112. A protrusion structure 113 is formed outwardly at one side of the base case 11 such that the nozzle cover 112 is disposed to be the liquid storage chamber 51 for storing the liquid. The nozzle cover 112 is a hollow structure extended toward the inner space from a top of the protrusion structure 113, and openings 1121 and 1122 are formed at two ends of the nozzle cover 112. The shape of the protrusion structure 113 is like a conical structure, but this disclosure is not limited thereto. Furthermore, in this embodiment, the base case 11 further comprises a communication pipe 114. The communication pipe 114 is configured at one side of the base case 11 as a part of the gas channel 24 for gas communication.

The lower case 12 is combinable with the base case 11. The lower case 12 comprises a nozzle 121 and a recess 122. In structural designs, the nozzle 121 is corresponding to the nozzle cover 112 of the base case 11, and the recess 122 is corresponding to the protrusion structure 113 of the base case 11. The nozzle 121 comprises an outlet portion 1211 and an inlet portion 1212 communicated with the pressurized gas source 500. A cross-section area of the outlet portion 1211 of the nozzle 121 is less than a cross-section area of the inlet portion 1212. When the lower case 12 is combined with the base case 11, the nozzle 121 passes through the opening 1122 of the nozzle cover 112 and is disposed in the nozzle cover 112 such that the outlet portion 1211 of the nozzle 121 is close to the opening 1121 of the nozzle cover 112. At this moment, a gap is formed between the nozzle cover 112 and the nozzle 121, and another gap is formed between the recess 122 of the lower case 12 and the protrusion structure 113 of the base case 11. The gaps are communicated with each other to be a part of the gas channel 24 for gas communication. One end of the gaps adjacent to the outlet portion 1211 of the nozzle 121 and the opening 1121 of the nozzle cover 112 forms an open end as the gas outlet 21, and the other end of the gaps is communicated with the communication pipe 114 of the base case 11 to form the gas channel 24. Furthermore, to prevent leakage of the gas from the junction of the base case 11 and the lower case 12, an adhesive sealing method or a sealing member is used at an outer edge of the junction of the base case 11 and the lower case 12 to provide an airtight effect of the gas channel 24, but this disclosure is not limited thereto.

The inner case 13 is configured in the inner space of the base case 11. The inner case 13 is a hollow structure, and the inner case 13 comprises a sleeve 131 sleeved on the nozzle cover 112. Two ends of the sleeve 131 form a top portion 1311 and a bottom portion 1312 with an opening respectively. When the inner case 13 is configured in the base case 11, the sleeve 131 is sleeved on the nozzle cover 112 and the opening of the top portion 1311 of the sleeve 131 is adjacent to the opening 1121 of the nozzle cover 112. At this moment, a gap is formed between the sleeve 131 and the nozzle cover 112, and another gap is formed between at least a part of the bottom portion 1312 of the sleeve 131 and the protrusion structure 113 of the base case 11. The gaps are communicated with each other to be a part of the liquid channel 52 for liquid communication. One end of the gaps adjacent to the opening of the top portion 1311 of the sleeve 131 and the opening 1121 of the nozzle cover 112 forms an open end as the liquid outlet 53, and the other end of the gaps is communicated with the liquid storage chamber 51. In this embodiment, the gas outlet 21 and the liquid outlet 53 are arranged at the same side of the outlet portion 1211. In other words, the gas outlet 21 and the liquid outlet 53 are arranged at the side with the outlet portion 1211 and are not arranged at an opposite side having the nebulization mechanism 40.

The upper cover 14 is combinable with the base case 11, and the inner case 13 is configured between the upper cover 14 and the base case 11. A gas space S communicated directly with the branch pipe 111 is formed in the upper cover 14 and the base case 11. The upper cover 14 comprises a first pressure relief hole 141, a second pressure relief hole 142 and at least one air inlet 143. The first pressure relief hole 141 and the second pressure relief hole 142 are used as the different gas inlet 22 of the closed pressure system 20, and the gas space S is communicated with the external air via the at least one air inlet 143.

The closed pressure system 20 of the nebulizer 1 of this disclosure further comprises an actuating element 25. The actuating element 25 is configured between the upper cover 14 and the inner case 13, such that an airtight chamber 23 of the closed pressure system 20 is formed between the upper cover 14 and the actuating element 25. In this embodiment, the actuating element 25 may be an elastically deformable airtight valve. The airtight chamber 23 and the gas space S are independent respectively, and the airtight chamber 23 is not directly gas communicated with the branch pipe 111. The airtight chamber 23 is capable of being communicated with the external air via the first pressure relief hole 141 and the second pressure relief hole 142. In this embodiment, the actuating element 25 comprises a fastening portion 251 and a through opening 252. The fastening portion 251 is connected to the nebulization mechanism 40, and the through opening 252 is communicated with the communication pipe 114 of the base case 11 to maintain the communication of the airtight chamber 23 and the gas channel 24.

In this embodiment, the at least one pressure relief mechanism 30 comprises a first pressure relief mechanism 31 and a second pressure relief mechanism 32. The first pressure relief mechanism 31 may be a cover disposed directly on the first pressure relief hole 141 to obstruct the communication of the airtight chamber 23 and the external air. The second pressure relief mechanism 32 may be a check valve. One side of the check valve is fastened on the upper cover 14, and the check valve covers normally the second pressure relief hole 142 and the at least one air inlet 143 to obstruct the communication of the airtight chamber 23 and the gas space S and the external air at the same time.

The nebulization mechanism 40 is disposed in the housing 10, and the nebulization mechanism 40 is connected to the actuating element 25. The nebulization mechanism 40 is actuatable to move to a nebulization position P1 or a non-nebulization position P2 by the actuating element 25. In this embodiment, the nebulization mechanism 40 may be a rod-like member, and two ends of the rod-like member are extended respectively toward the nozzle 121 and the upper cover 14. The nebulization mechanism 40 comprises a corresponding fastening portion 41 and a block portion 42. The block portion 42 is configured at the end of the rod-like member extended toward the nozzle 121, and the corresponding fastening portion 41 is connected to the fastening portion 251 of the actuating element 25.

As illustrated in FIG. 3 and FIG. 4, in this embodiment, when the inlet portion 1212 of the nozzle 121 is communicated with the pressurized gas source to introduce the pressurized gas, the pressurized gas is jetted from the outlet portion 1211 to produce a pressure difference. Because the gas outlet 21 and the liquid outlet 53 are both configured in the range of the pressure difference formed at the outlet portion 1211, the gas in the airtight chamber 23 is removed from the gas outlet 21 through the gas channel 24 by the pressure difference to decrease the interior gas pressure of the airtight chamber 23. Simultaneously, the liquid stored in the liquid storage chamber 51 is also drawn from the liquid outlet 53 through the liquid channel 52 by the pressure difference. Accordingly, the drawn liquid is moved with the pressurized gas toward the exterior of the outlet portion 1211.

Because the closed space is formed by the airtight chamber 23 and the gas channel 24, the actuating element 25 is shrunk toward the airtight chamber 23 by removal of the gas in the airtight chamber 23 and actuates the nebulization mechanism 40 to move to the non-nebulization position P2, such that the block portion 42 of the nebulization mechanism 40 is away from the outlet portion 1211, as shown in FIG. 4. Because the pressurized gas jetted from the outlet portion 1211 of the nozzle 121 is not blocked by the block portion 42 of the nebulization mechanism 40 and the liquid outlet 53 is outside of the outlet portion 1211 and the opening 1121, the pressure difference is not formed at the liquid outlet 53 by the pressurized gas jetted straightly along an axial direction of the nozzle 121 and the liquid is not drawn. In other words, when the nebulization mechanism 40 is at the non-nebulization position P2 in this embodiment, nebulization of the liquid cannot be produced by the nebulizer 1 of this disclosure. It should be noted that the liquid outlet 53 is capable of being in a range of the opening 1121 for different needs, such that the gas in the airtight chamber 23 and the liquid in the liquid storage chamber 51 are drawn together by the pressure difference.

If the nebulizer 1 of this disclosure is continuously maintained in the state shown in FIG. 4, then when the first pressure relief mechanism 31 or the second pressure relief mechanism 32 is changed to the opened state, the nebulization mechanism 40 is actuated to move to the nebulization position P1 from the non-nebulization position P2. For example, if the first pressure relief mechanism 31 is changed to the opened state (it means that the cover as the first pressure relief mechanism 31 is removed from the first pressure relief hole 141), the external air pressure is higher than the interior pressure of the airtight chamber 23. Therefore, the external air may be introduced into the airtight chamber 23 through the first pressure relief hole 141 to eliminate an airtight state of the airtight chamber 23 and increase the interior gas pressure of the airtight chamber 23. Once the interior gas pressure of the airtight chamber 23 is increased, the actuating element 25 is extended toward the outside of the airtight chamber 23 and actuates the nebulization mechanism 40 to move to the nebulization position P1 such that the block portion 42 of the nebulization mechanism 40 is close to the outlet portion 1211, as shown in FIG. 5A. In designs of this disclosure, an interval is maintained between the block portion 42 of the nebulization mechanism 40 at the nebulization position P1 and the outlet portion 1211, and the interval is in a distance range within which the liquid is capable of moving with the pressurized gas. In this state, the pressurized gas jetted from the outlet portion 1211 of the nozzle 121 is blocked by the block portion 42 of the nebulization mechanism 40 and flows radially at high speed such that a pressure difference is formed at the liquid outlet 53 to draw the liquid through the liquid channel 52. The drawn liquid is attracted to the outlet portion 1211 and impacts the block portion 42 with the pressurized gas to produce an aerosol through nebulization. In other words, when the nebulization mechanism 40 is at the nebulization position P1 in this embodiment, nebulization of the liquid is produced by the nebulizer 1 of this disclosure. Furthermore, nebulization of the liquid is produced continuously until the first pressure relief mechanism 31 is changed to the unopened state (it means that the first pressure relief hole 141 is covered by the cover as the first pressure relief mechanism 31).

On the other hand, if the nebulizer 1 of this disclosure is continuously maintained in the state as shown in FIG. 4, then when the patient inspires from the branch pipe 111, the gas in the gas space S is drawn and the check valve as the second pressure relief mechanism 32 is actuated to move toward the gas space S, such that the external air is capable of entering the gas space S from the at least one air inlet 143. At this moment, the second pressure relief hole 142 and the at least one air inlet 143 are not covered by the moved check valve, such that the external air is also capable of entering the airtight chamber 23 from the second pressure relief hole 142 because of the pressure difference. Therefore, the nebulization mechanism 40 is actuated to move to the nebulization position P1 based on the same principle for nebulization, as shown in FIG. 5B. The difference from the first pressure relief mechanism 31 is that once the patient exhales or stops inspiring, the check valve as the second pressure relief mechanism 32 is moved toward the outside of the gas space S, and the second pressure relief hole 142 and the at least one air inlet 143 are covered again by the check valve. The airtight chamber 23 forms the airtight state again, and the nebulization mechanism 40 is actuated to move to the non-nebulization position P2 by the pressure difference formed at the outlet portion 1211 by the pressurized gas, as shown in FIG. 4. In other words, the nebulizer 1 of this disclosure is capable of controlling the second pressure relief mechanism 32 with inspiration or exhalation of the patient in this embodiment, thereby providing a more humanized operation mode and reducing the waste of the liquid drug.

Figure 6:
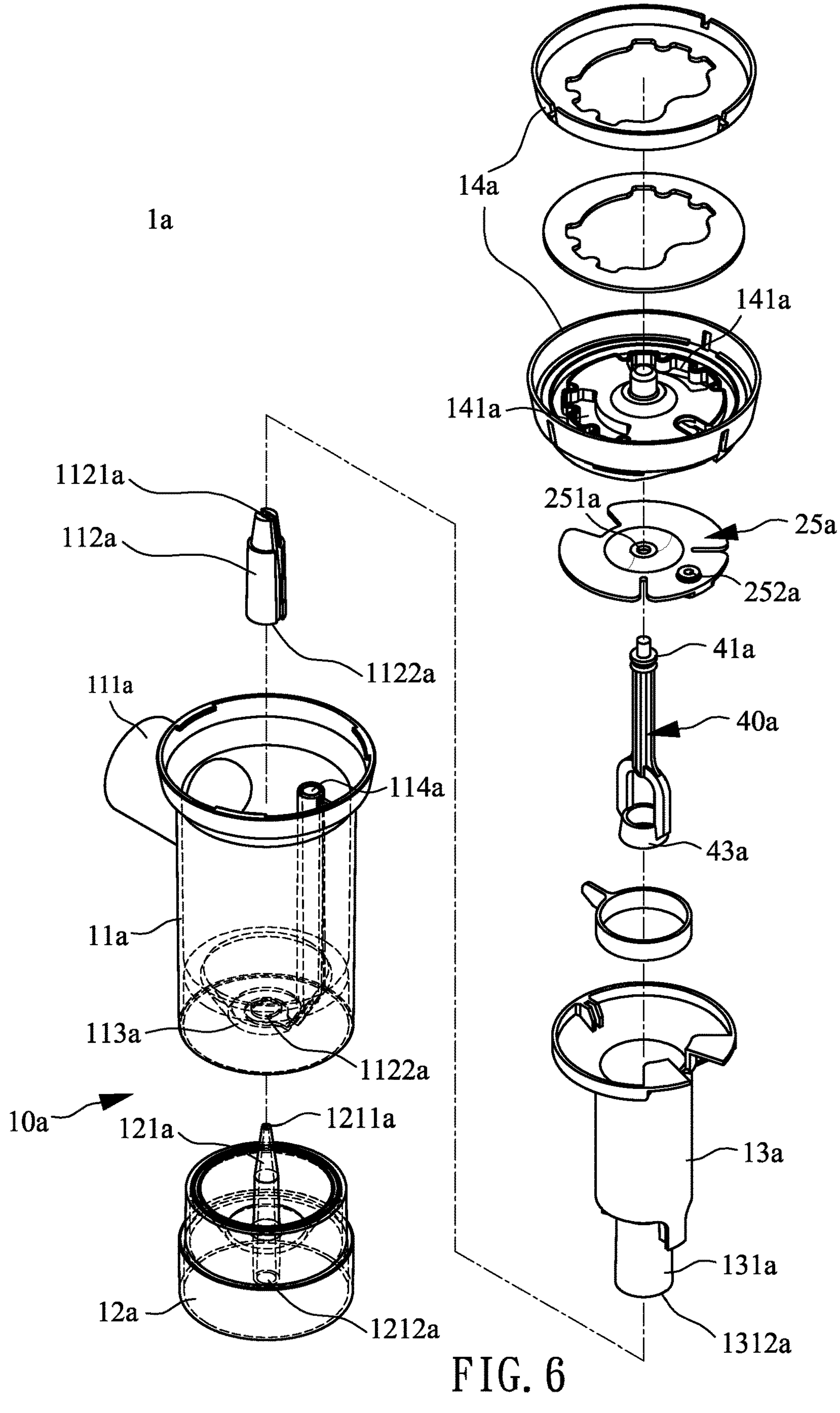
FIG. 6 illustrates an exploded view of a second embodiment of the nebulizer of this disclosure.
Figure 7A:
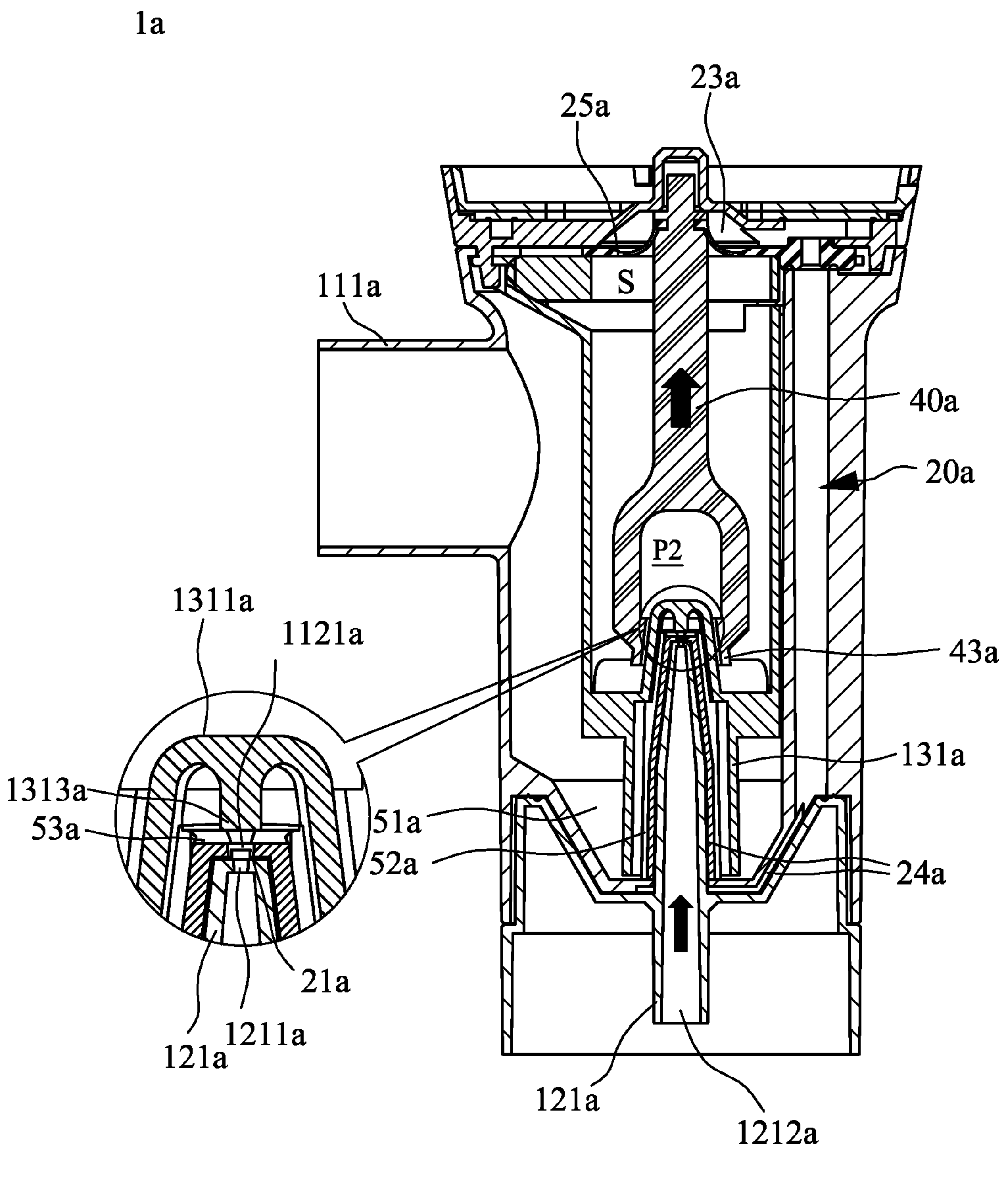
FIGS. 7A-7B illustrate cross-sectional views of the nebulization mechanism of the second embodiment of the nebulizer of this disclosure at the non-nebulization position.
Figure 7B:
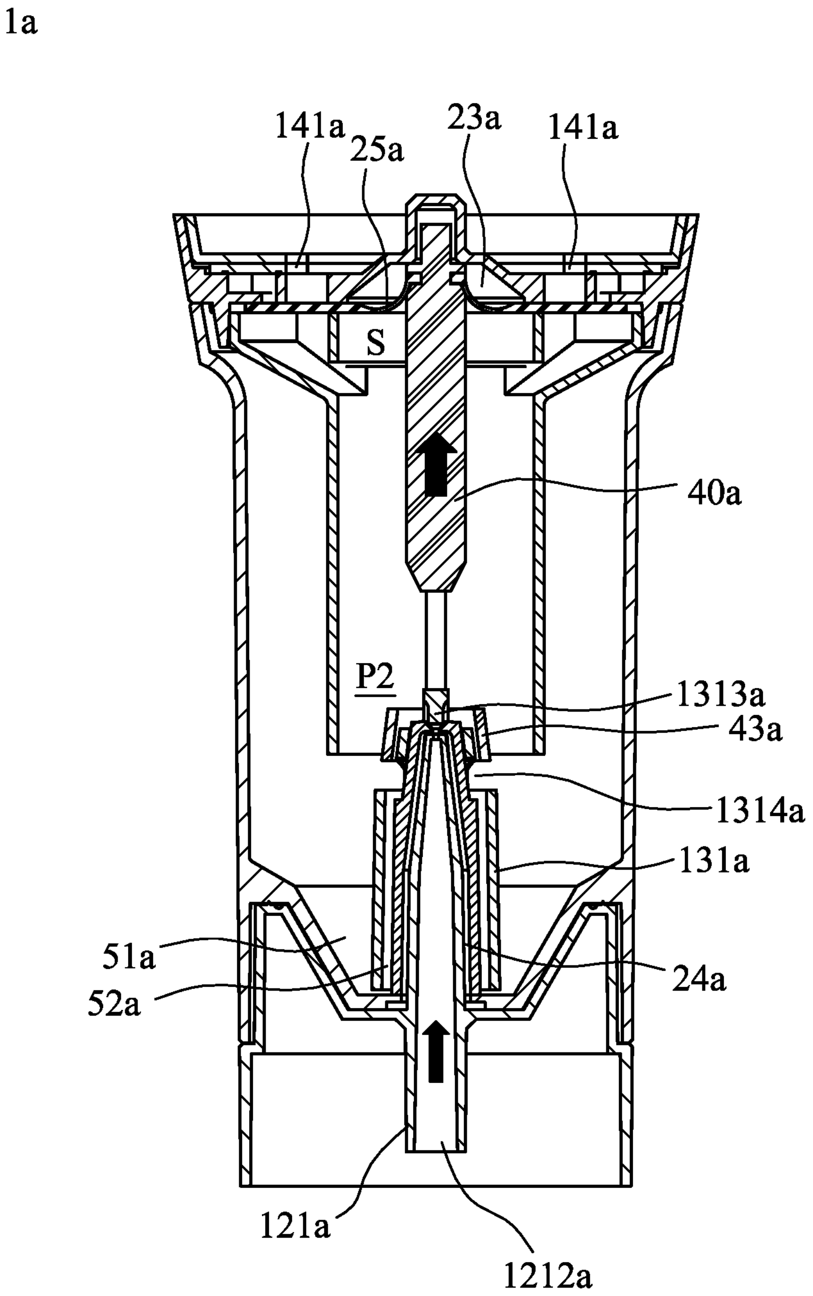
Figure 8:
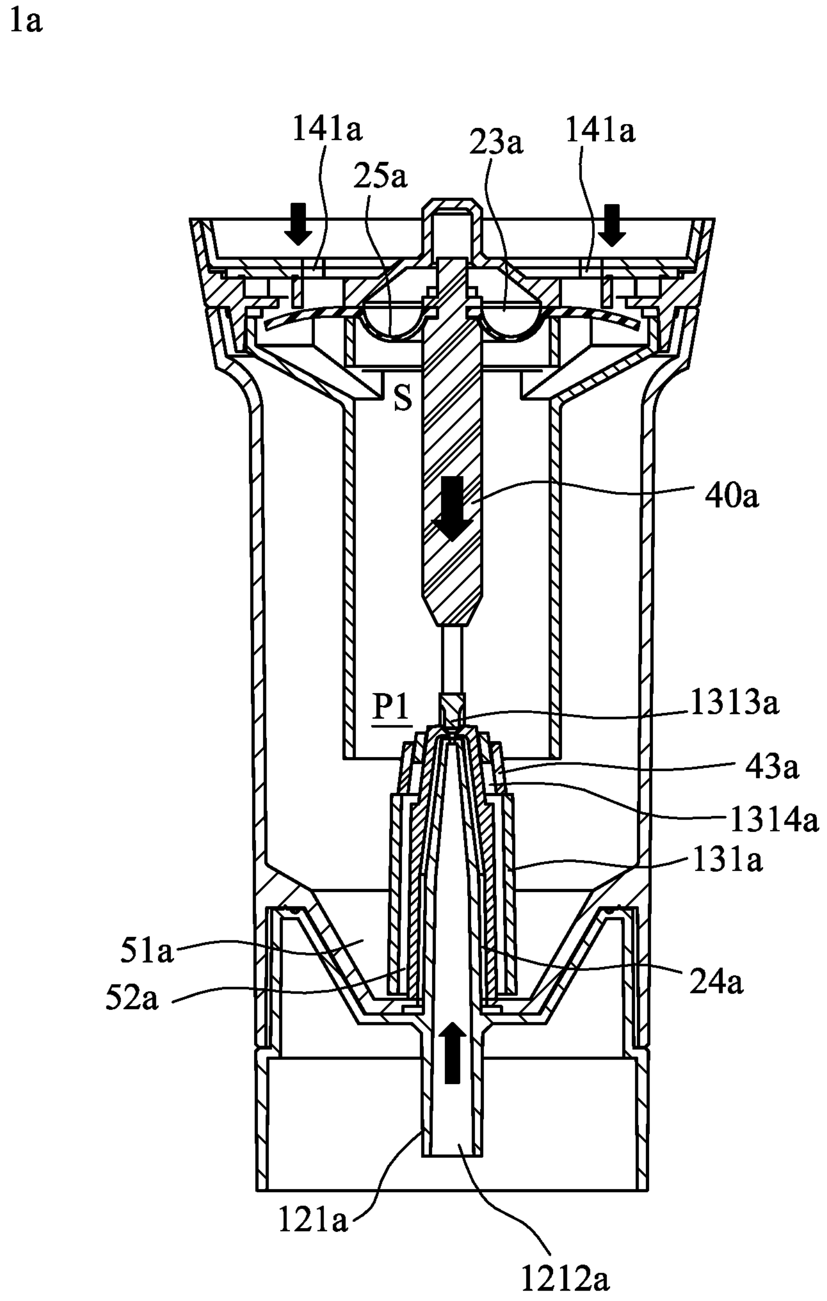
FIG. 8 illustrates a cross-sectional view of the nebulization mechanism of the second embodiment of the nebulizer of this disclosure at the nebulization position.

Please refer to FIG. 6 to FIG. 8. FIG. 6 illustrates an exploded view of a second embodiment of the nebulizer 1*a* of this disclosure, FIGS. 7A-7B illustrate cross-sectional views of the nebulization mechanism of the second embodiment of the nebulizer 1*a* of this disclosure at the non-nebulization position, and FIG. 8 illustrates a cross-sectional view of the nebulization mechanism of the second embodiment of the nebulizer 1*a* of this disclosure at the nebulization position. As illustrated in FIG. 6 to FIG. 8, the second embodiment of the nebulizer 1*a* of this disclosure is a variation of the aforementioned first embodiment. In this embodiment, the nebulizer 1*a* of this disclosure comprises a housing 10*a*, a closed pressure system 20*a*, a pressure relief mechanism and a nebulization mechanism 40*a*. The housing 10*a* comprises a base case 11*a*, a lower case 12*a*, an inner case 13*a* and an upper cover 14*a*. Since the structural designs of the base case 11*a* and the lower case 12*a* are similar to those of the aforementioned embodiment, they are not further described herein.

In this embodiment, the inner case 13*a* is configured in the inner space of the base case 11*a*. The inner case 13*a* is a hollow structure, and the inner case 13*a* comprises a sleeve 131*a* sleeved on the nozzle cover 112*a*. Two ends of the sleeve 131*a* form a top portion 1311*a* and a bottom portion 1312*a* with an opening respectively, and a baffle 1313*a* is disposed at the top portion 1311*a*. The baffle 1313*a* is used for blocking the liquid moved with the pressurized gas. When the inner case 13*a* is configured in the base case 11*a*, the sleeve 131*a* is sleeved on the nozzle cover 112*a*, and the opening of the top portion 1311*a* of the sleeve 131*a* is adjacent to the outlet portion 1211*a* of the nozzle 121*a*. The baffle 1313*a* of the sleeve 131*a* is at a position above the outlet portion 1211*a* of the nozzle 121*a* and the opening 1121*a* of the nozzle cover 112*a*, and an interval is maintained between the baffle 1313*a* and the outlet portion 1211*a* of the nozzle 121*a*. The interval is in the distance range within which the liquid is capable of moving with the pressurized gas. At this moment, a gap is formed between the sleeve 131*a* and the nozzle cover 112*a*, and another gap is formed between at least a part of the bottom portion 1312*a* of the sleeve 131*a* and the protrusion structure 113*a* of the base case 11*a*. The gaps are communicated with each other to be a part of the liquid channel 52*a* for liquid communication. One end of the gaps adjacent to the opening of the top portion 1311*a* of the sleeve 131*a* and the outlet portion 1211*a* of the nozzle 121*a* forms an open end as the liquid outlet 53*a*, and the other end of the gaps is communicated with the liquid storage chamber 51*a*.

Furthermore, the sleeve 131*a* further comprises a liquid relief opening 1314*a*. The liquid relief opening 1314*a* is configured between the top portion 1311*a* and the bottom portion 1312*a*, and the liquid channel 52*a* is directly communicated with the inner space in the base case 11*a* by the liquid relief opening 1314*a*.

The upper cover 14*a* is combinable with the base case 11*a*, and the inner case 13*a* is configured between the upper cover 14*a* and the base case 11*a*. A gas space S communicated directly with the branch pipe 111*a* is formed in the upper cover 14*a*. In this embodiment, the upper cover 14*a* comprises at least one pressure relief hole 141*a*. The pressure relief hole 141*a* is used as the gas inlet of the closed pressure system 20*a*, and the gas space S is communicated with the external air via the at least one pressure relief hole 141*a*. In other words, the at least one pressure relief hole 141*a* has the functions of the pressure relief hole and the air inlet of the aforementioned first embodiment.

The nebulizer 1*a* of this disclosure further comprises an actuating element 25*a*. The actuating element 25*a* is configured between the upper cover 14*a* and the inner case 13*a* such that an airtight chamber 23*a* is formed between the upper cover 14*a* and the actuating element 25*a*. The airtight chamber 23*a* and the gas space S are independent respectively, and the airtight chamber 23*a* is not directly gas communicated with the branch pipe 111*a*. The airtight chamber 23*a* is capable of being communicated with the external air via the at least one pressure relief hole 141*a*. In this embodiment, the actuating element 25*a* comprises a fastening portion 251*a* and a through opening 252*a*. The fastening portion 251*a* is connected to the nebulization mechanism 40*a*, and the through opening 252*a* is communicated with the communication pipe 114*a* of the base case 11*a* to maintain the communication of the airtight chamber 23*a* and the gas channel 24*a*.

In this embodiment, the actuating element 25*a* is capable of replacing the pressure relief mechanism 30 of the aforementioned first embodiment. The actuating element 25*a* may cover directly the at least one pressure relief hole 141*a* to obstruct the communication of the gas space S and the airtight chamber 23*a* and the external air.

The nebulization mechanism 40*a* is disposed in the housing 10*a*, and the nebulization mechanism 40*a* is connected to the actuating element 25*a*. The nebulization mechanism 40*a* is actuatable to move to a nebulization position P1 or a non-nebulization position P2 by the actuating element 25*a*. In this embodiment, the nebulization mechanism 40*a* may be a rod-like member, and two ends of the rod-like member are extended respectively toward the nozzle 121*a* and the upper cover 14*a*. The nebulization mechanism 40*a* comprises a corresponding fastening portion 41*a* and a closed portion 43*a*. The closed portion 43*a* is configured at the end of the rod-like member extended toward the nozzle 121*a* for covering the liquid relief opening 1314*a* of the sleeve 131*a*, and the corresponding fastening portion 41*a* is connected to the fastening portion 251*a* of the actuating element 25*a*.

As illustrated in FIG. 6 to FIG. 8, in this embodiment, when the outlet portion 1211*a* of the nozzle 121*a* is communicated with the pressurized gas source to introduce the pressurized gas, the pressurized gas is jetted from the outlet portion 1211*a* to produce a pressure difference. Because the gas outlet 21*a* and the liquid outlet 53*a* are both configured in the range of the pressure difference formed at the outlet portion 1211*a*, the gas in the airtight chamber 23*a* is removed from the gas outlet 21*a* through the gas channel 24*a* by the pressure difference to decrease the interior gas pressure of the airtight chamber 23*a*.

Because the closed space is formed by the airtight chamber 23*a* and the gas channel 24*a*, the actuating element 25*a* is shrunk toward the airtight chamber 23*a* by removal of the gas in the airtight chamber 23*a* and actuates the nebulization mechanism 40*a* to move to the non-nebulization position P2 such that the closed portion 43*a* of the nebulization mechanism 40*a* is away from the liquid relief opening 1314*a* of the sleeve 131*a*, as shown in FIGS. 7A-7B. At this moment, the liquid relief opening 1314*a* is exposed to relief pressure and the airtight state of the liquid channel 52*a* is eliminated such that the liquid cannot be transmitted to the liquid outlet 53*a* so as to obstruct the liquid channel 52*a*. Therefore, the pressurized gas without any liquid is jetted from the outlet portion 1211*a* of the nozzle 121*a*. In other words, when the nebulization mechanism 40*a* is at the non-nebulization position P2 in this embodiment, the liquid channel 52*a* is obstructed and nebulization of the liquid cannot be produced by the nebulizer 1*a* of this disclosure.

If the nebulizer 1*a* of this disclosure is continuously maintained in the state as shown in FIGS. 7A-7B, then when the patient inspires from the branch pipe 111*a*, the gas in the gas space S is drawn and the actuating element 25*a* is actuated to move toward the gas space S such that the at least one pressure relief hole 141*a* is not covered by the actuating element 25*a*. At this moment, the gas space S is communicated with the airtight chamber 23*a* by the moved actuating element 25*a*, and the external air is capable of entering the gas space S and the airtight chamber 23*a* from the at least one pressure relief hole 141*a*. Therefore, the nebulization mechanism 40*a* is actuated to move to the nebulization position P1 based on the same principle, as shown in FIG. 8. At this moment, the nebulization mechanism 40*a* at the nebulization position P1 covers the liquid relief opening 1314*a* of the sleeve 131*a* via the closed portion 43*a*, and the airtight state of the liquid channel 52*a* is recovered, such that the liquid in the liquid storing chamber 51*a* is drawn through the liquid channel 52*a* from the liquid outlet 53*a* by the pressure difference formed at the outlet portion 1211*a*. The drawn liquid impacts the baffle 1313*a* of the sleeve 131*a* with the pressurized gas to be nebulized into an aerosol. Similarly, once the patient exhales or stops inspiring, the actuating element 25*a* is moved toward the outside of the gas space S and the at least one pressure relief hole 141*a* is covered again by the actuating element 25*a*. The airtight chamber 23*a* forms the airtight state again, and the nebulization mechanism 40*a* is actuated to move to the non-nebulization position P2 by the pressure difference formed at the outlet portion 1211*a* by the pressurized gas, as shown in FIGS. 7A-7B.

Figure 9:
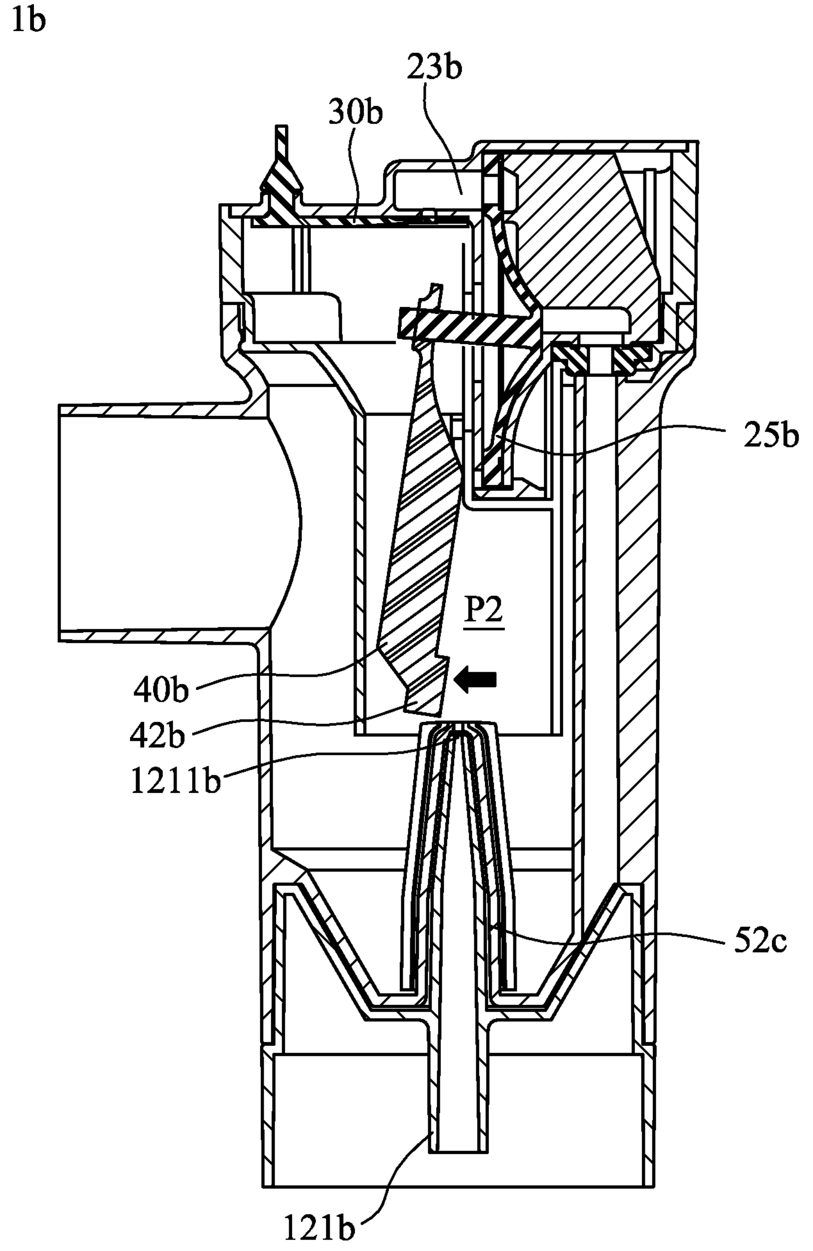
FIG. 9 illustrates a cross-sectional view of the nebulization mechanism of a third embodiment of the nebulizer of this disclosure at the non-nebulization position.
Figure 10:
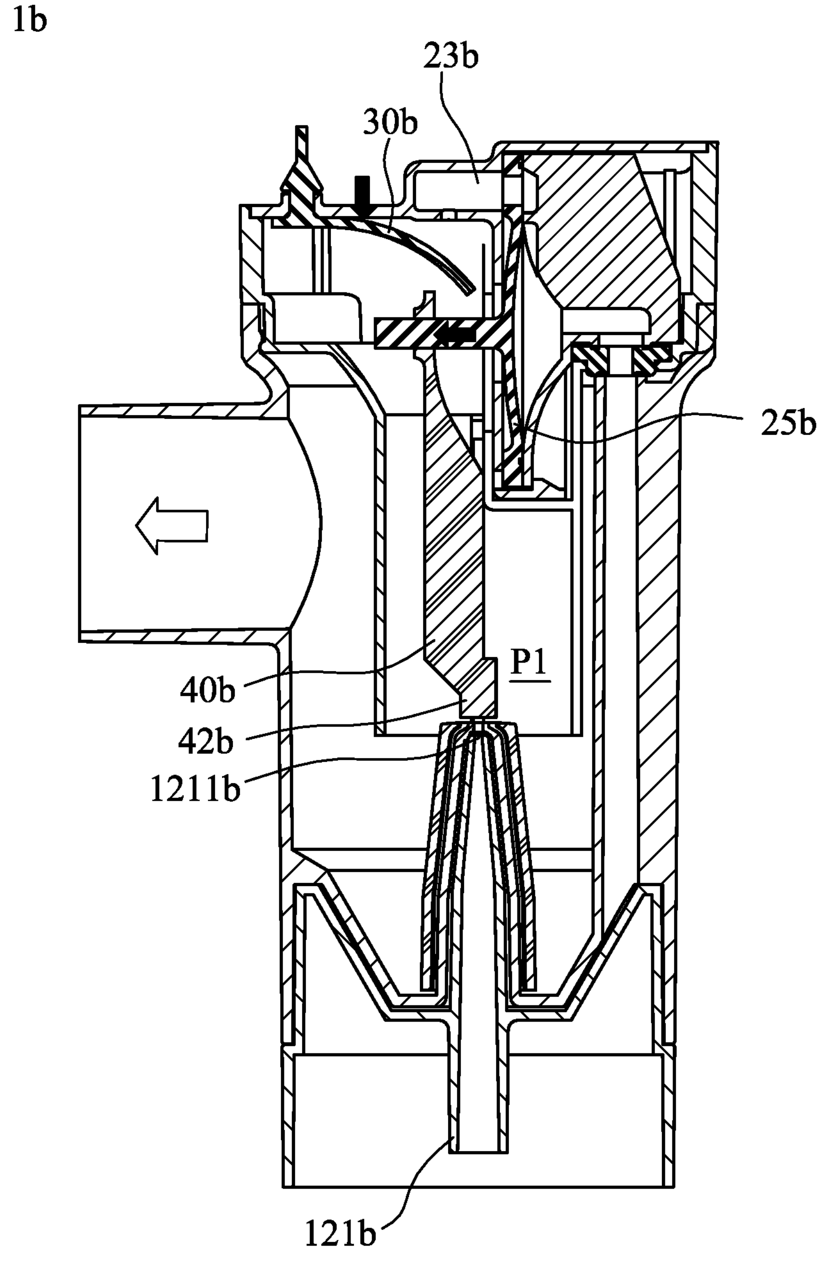
FIG. 10 illustrates a cross-sectional view of the nebulization mechanism of the third embodiment of the nebulizer of this disclosure at the nebulization position.

Please refer to FIG. 9 and FIG. 10. FIG. 9 illustrates a cross-sectional view of the nebulization mechanism of a third embodiment of the nebulizer 1*b* of this disclosure at the non-nebulization position, and FIG. 10 illustrates a cross-sectional view of the nebulization mechanism of the third embodiment of the nebulizer 1*b* of this disclosure at the nebulization position. As illustrated in FIG. 9 and FIG. 10, the third embodiment of the nebulizer 1*b* of this disclosure is a variation of the aforementioned first embodiment. In this embodiment, the linkage operation of the actuating element 25*b* and the nebulization mechanism 40*b* of the nebulizer 1*b* of this disclosure is changed. The actuating element 25*b* moves transversely to push the nebulization mechanism 40*b* such that the nebulization mechanism 40*b* is shifted transversely from a position over the outlet portion 1211*b* of the nozzle 121*b* when the pressure relief mechanism 30*b* is changed to the unopened state. At this moment, the liquid jetted with the pressurized gas is not blocked by the block portion 42*b* of the nebulization mechanism 40*b*. Oppositely, when the pressure relief mechanism 30*b* is changed to the opened state, the nebulization mechanism 40*b* is actuated to move to the position over the outlet portion 1211*b* of the nozzle 121*b* according to the pressure change of the airtight chamber 23*b*. At this moment, the liquid jetted with the pressurized gas is blocked by the block portion 42*b* of the nebulization mechanism 40*b* for nebulization.

Figure 11:
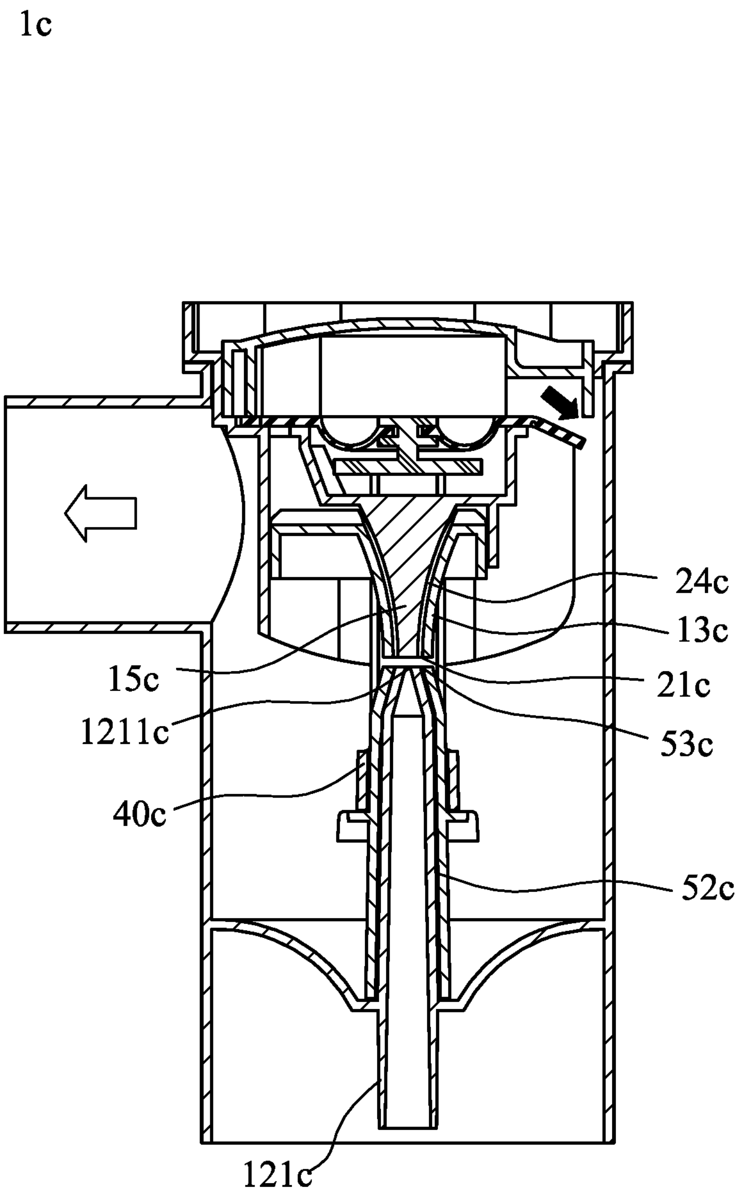
FIG. 11 illustrates a cross-sectional view of the nebulization mechanism of a fourth embodiment of the nebulizer of this disclosure at the nebulization position.

Please refer to FIG. 11, which illustrates a cross-sectional view of the nebulization mechanism of a fourth embodiment of the nebulizer of this disclosure at the nebulization position. As illustrated in FIG. 11, the fourth embodiment of the nebulizer 1*b* of this disclosure is a variation of the aforementioned second embodiment. In this embodiment, the design of the inner case 13*c* of the nebulizer 1*c* of this disclosure is changed such that the assembly of the gas channel 24*c* formed by the inner case 13*c* in conjunction with a structural component 15*c* above the inner case 13*c* is configured relative to the nozzle 121*c*. In other words, the outlet portion 1211*c* of the nozzle 121*c* and the liquid outlet 53*c* are arranged at the same side having the nozzle 121*c*, and the gas outlet 21*c* is arranged at the opposite side for the nozzle 121*c*. Accordingly, the length of the gas channel 24*c* may be substantially reduced, and the gas channel 24*c* is obviously separated from the liquid channel 52*c*. Therefore, the nebulization mechanism 40*c* is actuated to obstruct or communicate with the liquid channel 52*c* by the pressure difference formed at the outlet portion 1211*c*.

In other words, this disclosure further discloses a nebulizer in communication with a pressurized gas source and storing a liquid. The nebulizer comprises a differential pressure forming structure, an airtight unit and a nebulization mechanism. The differential pressure forming structure is used for inputting a pressurized gas from the pressurized gas source and forming a pressure difference at an outlet portion. The airtight unit is in gas communication with the outlet portion. The nebulization mechanism is capable of moving relative to the outlet portion of the differential pressure forming structure. The airtight unit is configured to actuate the nebulization mechanism in response to the pressure difference. The nebulizer of this disclosure further comprises a liquid transmission unit. The liquid transmission unit is in liquid communication with a position adjacent to the outlet portion, and the liquid transmission unit is configured to transmit the liquid to the outlet portion by the pressurized gas in the presence of the pressure difference. The airtight unit and the liquid transmission unit are not communicated with each other. The gas is removed from the airtight unit by the pressure difference, and an interior gas pressure of the airtight unit is maintained as a first pressure. The airtight unit further comprises at least one pressure relief mechanism for releasing the interior gas pressure of the airtight unit to a second pressure. In one embodiment of this disclosure, the first pressure is less than the second pressure, but this disclosure is not limited thereto.

In summary, the interior pressure of the nebulizer of this disclosure is changeable according to the breathing of the patient to control the nebulization mechanism such that nebulization of the liquid is produced with inspiration of the patient. Accordingly, the necessity of manual operation is reduced by using the nebulizer of this disclosure, and the usage amount of the liquid drug may be effectively saved to reduce resource waste.

The above detailed description is merely illustrative in nature and is not intended to limit the embodiments of the subject matter or the application and uses of such embodiments. Moreover, although at least one exemplary embodiment has been presented in the foregoing detailed description, it should be appreciated that a vast number of variations exist. It should also be appreciated that the exemplary one or more embodiments described herein are not intended to limit the scope, applicability, or configuration of the claimed subject matter in any way. Rather, the foregoing detailed description will provide those skilled in the art with a convenient guide for implementing the described one or more embodiments. Also, various changes can be made to the function and arrangement of elements without departing from the scope defined by the claims, which include known equivalents and foreseeable equivalents at the time of filing of this patent application.

What is claimed is:

1. A nebulizer, comprising:

a housing comprising:

a nozzle having an inlet portion which is configured to communicate with a pressurized gas source for introducing a pressurized gas into the nozzle, and an outlet portion which is disposed downstream of the inlet portion so as to produce a pressure difference when the pressurized gas is discharged from the outlet portion; and a liquid outlet disposed for outputting a liquid, and located within a range of the pressure difference so as to permit the liquid to be drawn by the pressure difference to flow out of the liquid outlet and to be entrained in the pressurized gas;

a chamber unit disposed in the housing and comprising at least one gas inlet for introducing an external gas, and a gas outlet located within the range of the pressure difference;

at least one pressure relief mechanism disposed on the at least one gas inlet to switch the at least one gas inlet between:

an unopened state, where the external gas is prevented from being introduced into the chamber unit to permit an interior gas of the chamber unit to be drawn by the pressure difference to flow out of the gas outlet, to thereby decrease an internal pressure inside the chamber unit; and an opened state, where the external gas is permitted to be introduced into the chamber unit to increase the internal pressure inside the chamber unit;

an actuating element coupled to move in response to a variation of the internal pressure inside the chamber unit; and a nebulization mechanism coupled to the actuating element such that:

when the at least one pressure relief mechanism is in the unopened state to cause decreasing of the internal pressure, the nebulization mechanism is positioned by the actuating element at a non-nebulization position, where the nebulization mechanism is distal from the outlet portion, to thereby prevent the liquid entrained in the pressurized gas from impacting the nebulization mechanism; and when the at least one pressure relief mechanism is in the opened state to cause increasing the internal pressure, the nebulization mechanism is positioned by the actuating element at a nebulization position, where the nebulization mechanism is proximate to the outlet portion, to thereby allow the liquid entrained in the pressurized gas to impact the nebulization mechanism to produce an aerosol.

2. The nebulizer of claim 1, wherein the chamber unit further comprises:

an airtight chamber disposed downstream of the at least one gas inlet; and a gas channel interconnecting the gas outlet and the airtight chamber so as to permit the airtight chamber to be in fluid communication with the gas outlet via the gas channel.

3. The nebulizer of claim 2, wherein the housing further comprises a liquid storage chamber for storing the liquid;

a liquid channel disposed to interconnect the liquid storage chamber with the liquid outlet so as to permit the liquid in the liquid storage chamber to be drawn by the pressure difference to flow out of the liquid outlet through the liquid channel; and a separator disposed between the gas channel and the liquid channel so as to separate the gas channel from the liquid channel.

4. The nebulizer of claim 3, wherein the gas outlet and the liquid outlet are arranged at the same side of the outlet portion.

5. The nebulizer of claim 3, wherein the nebulization mechanism comprises a block portion, and wherein when the nebulization mechanism moves to the nebulization position, the liquid entrained in the pressurized gas is permitted to impact the block portion to produce the aerosol.

6. The nebulizer of claim 1, wherein the actuating element is capable of maintaining the nebulization mechanism at the nebulization position when the pressure difference is produced.

7. The nebulizer of claim 1, wherein the gas outlet is in a ring shape to surround the outlet portion and is located above the outlet portion.

8. The nebulizer of claim 1, wherein the housing further comprises a branch pipe configured such that in response to a suction force applied to the branch pipe, the pressure relief mechanism is switched to the opened state, to thereby permit the nebulization mechanism to be driven by the actuating element to the nebulization position.

9. The nebulizer of claim 1, wherein the actuating element is an elastically deformable element such that when the pressure relief mechanism is in the unopened state, the actuating element is deformed by the decreased internal pressure to pull the nebulization mechanism away from the outlet portion to the non-nebulization position, and such that when the pressure relief mechanism is in the opened state, the actuating element is released to cause movement of the nebulization mechanism to the nebulization position.

10. A nebulizer, comprising:

a nozzle having:

an inlet portion configured to communicate with a pressurized gas source for introducing a pressurized gas into the nozzle; and an outlet portion having a reduced dimension relative to the inlet portion so as to produce a pressure difference when the pressurized gas is discharged from the outlet portion;

a liquid outlet disposed for outputting a liquid, and located within a range of the pressure difference so as to permit the liquid to be drawn by the pressure difference to flow out of the liquid outlet and to be entrained in the pressurized gas;

a chamber unit including a gas outlet located within the range of the pressure difference;

an actuating element coupled to move in response to a variation of an internal pressure inside the chamber unit; and a nebulization mechanism coupled to the actuating element such that when an interior gas of the chamber unit is drawn by the pressure difference to flow out of the gas outlet to decrease the internal pressure, the nebulization mechanism is driven by the actuating element to move from a nebulization position, where the nebulization mechanism is proximate to the outlet portion to permit the liquid entrained in the pressurized gas to impact the nebulization mechanism to form an aerosol, to a non-nebulization position, where the nebulization mechanism is distal from the outlet portion to prevent the liquid entrained in the pressurized gas from impacting the nebulization mechanism.

11. A breath-actuated nebulization method, comprising:

providing the nebulizer according to claim 10;

introducing the pressurized gas from the inlet portion of the nozzle and producing a pressure difference at the outlet portion of the nozzle;

removing gas from the chamber unit in the housing via a gas channel by the pressure difference to decrease an interior gas pressure of the chamber unit; and introducing air into the chamber unit with inspiration to increase the interior gas pressure of the chamber unit such that the liquid is drawn through a liquid channel by the pressure difference.

12. The method of claim 11, wherein the liquid impacts the nebulization mechanism along with the pressurized gas to produce the aerosol.

13. The method of claim 12, wherein the nebulization mechanism moves close to the outlet portion to nebulize the liquid into the aerosol when the nebulization mechanism moves to the nebulization position from the non-nebulization position, and wherein the nebulization mechanism moves away from the outlet portion when the nebulization mechanism moves to the non-nebulization position from the nebulization position.

14. The method of claim 12, wherein the air is introduced into the chamber unit by a pressure relief mechanism.

15. A nebulizer comprising:

a housing formed with a gas space, and including a nozzle with an outlet portion which is configured for discharging a pressurized gas and which is in spatial communication with the gas space;

a pressure system having an actuating element, and defining:

an enclosed space located within the gas space; and a gas outlet which is in spatial communication with the outlet portion and which is located within a range where a pressure difference is produced when the pressurized gas is discharged from the outlet portion; and a nebulization mechanism connected to the actuating element and capable of moving by the actuating element relative to the outlet portion of the nozzle, wherein the pressure system is configured such that when the pressurized gas is discharged from the outlet portion to produce the pressure difference, an interior gas of the enclosed space of the pressure system is drawn by the pressure difference to flow out of the gas outlet, to thereby allow the nebulization mechanism to be actuated by the actuating element to move and be positioned at a non-nebulization position.

16. The nebulizer of claim 15, wherein the housing further comprises a nozzle cover which defines, together with the nozzle, an elongated gap that extends upwardly to terminate at an upper opening, the upper opening being in spatial communication with the gas space and being located above the outlet portion to serve as the gas outlet.

* * * * *